(12) United States Patent
Nikawa et al.

(10) Patent No.: US 9,138,507 B2
(45) Date of Patent: Sep. 22, 2015

(54) METHOD FOR MANUFACTURING AN IMPLANT MATERIAL

(71) Applicant: Toyo Advanced Technologies Co., Ltd., Hiroshima-shi (JP)

(72) Inventors: Hiroki Nikawa, Hiroshima (JP); Seichiyou Makihira, Hiroshima (JP); Yuichi Mine, Hiroshima (JP); Yoshinori Abe, Hiroshima (JP); Tatsuyuki Nakatani, Hiroshima (JP); Keishi Okamoto, Hiroshima (JP); Yuki Nitta, Hiroshima (JP)

(73) Assignee: TOYO ADVANCED TECHNOLOGIES CO., LTD., Hiroshima-Shi (JP)

(*) Notice: Subject to any disclaimer, the term of this patent is extended or adjusted under 35 U.S.C. 154(b) by 0 days.

(21) Appl. No.: 14/538,664

(22) Filed: Nov. 11, 2014

(65) Prior Publication Data
US 2015/0064339 A1    Mar. 5, 2015

Related U.S. Application Data

(62) Division of application No. 13/148,928, filed as application No. PCT/JP2009/000541 on Feb. 10, 2009.

(51) Int. Cl.
*A61L 27/02* (2006.01)
*A61L 27/30* (2006.01)
(Continued)

(52) U.S. Cl.
CPC .............. *A61L 27/025* (2013.01); *A61K 6/027* (2013.01); *A61L 27/303* (2013.01); *A61L 27/306* (2013.01); *C23C 16/30* (2013.01); *A61L 2420/04* (2013.01); *Y10T 428/31678* (2015.04)

(58) Field of Classification Search
CPC .... C23C 14/00; C23C 14/221; C23C 14/548; C23C 16/00; C23C 16/30; A61L 27/025; A61L 27/303; A61K 6/027
See application file for complete search history.

(56) References Cited

U.S. PATENT DOCUMENTS 5,062,798 A    11/1991  Tsuge et al.
5,551,959 A  *  9/1996  Martin et al. .................. 51/295
(Continued)

FOREIGN PATENT DOCUMENTS

EP    2018881 A1   1/2009
JP    2002-204825 A   7/2002
(Continued)

OTHER PUBLICATIONS

Bendavid et al., The mechanical and biocompatibility properties of DLC-Si films prepared by pulsed DC plasma activated chemical vapor deposition, Diamond and Related Materials, 2007, pp. 1616-1622, vol. 16.
(Continued)

*Primary Examiner* — Moshe Wilensky
(74) *Attorney, Agent, or Firm* — Knobbe Martens Olson & Bear LLP

(57) ABSTRACT

A method for manufacturing an implant material includes preparing a base material for implant, removing moisture from a chamber in which the base material is placed, and introducing material gas as a carbon source and a silicon source into the chamber after the removal of the moisture to form a carbon thin film containing a C—C component in which carbon atoms are bonded, and a SiC component in which carbon and silicon atoms are bonded on a surface of the base material by ionized deposition.

5 Claims, 4 Drawing Sheets

(51) Int. Cl.
*C23C 16/30* (2006.01)
*A61K 6/027* (2006.01)

(56) References Cited

U.S. PATENT DOCUMENTS

| | | | |
|---|---|---|---|
| 5,605,714 A | 2/1997 | Dearnaley et al. | |
| 2006/0150862 A1* | 7/2006 | Zhao et al. | 106/286.1 |
| 2006/0269901 A1 | 11/2006 | Rosenblood et al. | |

FOREIGN PATENT DOCUMENTS

| | | | |
|---|---|---|---|
| JP | 2005-013719 A | 1/2005 | |
| JP | 2005-168936 | 6/2005 | |
| JP | 2006-000219 A | 1/2006 | |
| JP | 2006-000521 A | 1/2006 | |
| JP | 2007-097844 A | 4/2007 | |
| JP | 2009-120885 A | 6/2009 | |
| WO | WO 00/47290 A1 | 8/2000 | |
| WO | WO 2004/006977 A2 | 1/2004 | |
| WO | WO 2008125607 A2 * | 10/2008 | |

OTHER PUBLICATIONS

Kim et al., Effect of Si-incorporation on wear-corrosion properties of diamond-like carbon films, Thin Solid Films, 2005, pp. 299-304, vol. 482.

Liu et al., Reduction of bacterial adhesion on modified DLC coatings, Colloids and Surfaces B: Biointerfaces, 2008, pp. 182-187, vol. 61.

Liu et al., In vitro electrochemical corrosion behavior of functionally graded diamond-like carbon coatings on biomedical Nitinol alloy, Thin Solid Films, 2006, pp. 457-462, vol. 496.

Muhlbradt et al., Mechanoperception of natural teeth versus endosseous implants revealed by magnitude estimation, Int Oral Maxillofac Implants, 1989, pp. 125-130, vol. 4.

Zhao et al., Evaluation of bacterial adhesion on Si-doped diamond-like carbon films, Applied Surface Science, 2007, pp. 7254-7259, vol. 253.

Cheng, Qijin et al., Homogeneous nanocrystalline cubic silicon carbide films prepared by inductively coupled plasma chemical vapor deposition, Nanotechnology, Oct. 12, 2007, vol. 18, IOP Publishing Ltd, UK.

Roy, Ritwik et al., Surface energy of the plasma treated Si incorporated diamond-like carbon films, Diamond & Related Materials, Jun. 21, 2007, vol. 16, Elsevier B. V.

Database WPI, Week 200512, Thomas Scientific, London, GB; AN 2005-105000, XP002696276.

Supplementary European Search Report dated May 14, 2013 in corresponding Application No. 09839942.1.

Takabayashi et al., Surface analysis of carbon-hydrogen bonds in diamondlike carbon films by X-ray photoelectron spectroscopy, Japanese Journal of Applied Physics, 48, Sep. 24, 2009.

* cited by examiner

METHOD FOR MANUFACTURING AN IMPLANT MATERIAL

CROSS-REFERENCE TO RELATED APPLICATIONS

This application is a divisional of U.S. application Ser. No. 13/148,928, filed on Aug. 10, 2011 as the U.S. National Phase under 35 U.S.C. §371 of International Application PCT/JP2009/000541, filed Feb. 10, 2009, which is hereby incorporated by reference in their entirety. Japanese Patent Application No. 2007-316095 is another prior foreign application for which priority is not claimed. The entire disclosure of this prior foreign application is also incorporated by reference in its entirety.

TECHNICAL FIELD

The present disclosure relates to implant materials and a method for manufacturing the same, particularly to dental materials to which affinity for bone cells is required, such as dental implants, artificial teeth, etc., and a method for manufacturing the same.

BACKGROUND ART

Titanium and titanium alloys have been used as base materials of implants which are placed in living bodies, such as dental implants, for their high biocompatibility, resistance to corrosion, and mechanical strength. However, when a dental implant made of titanium and the titanium alloy is directly fixed to a jaw bone, metabolism in restoring osseous tissue of the jaw bone gets out of balance, and the dental implant may be loosened, or osteolysis of the jaw bone may occur.

A cause of the dental implant failure is peri-implantitis which may lead to osteolysis by osteoclasts induced around the dental implant. The peri-implantitis may be derived from microbial stimulus such as bacterial infection etc., and mechanical stimulus such as excessive occlusal force etc., and may also be caused by activation of the osteoclasts by the dental implant itself.

The activation of the osteoclasts by the dental implant occurs in an early stage after the placement of the implant. The osteoclasts induced in the early stage inhibit osseointegration of the implant, which leads to implant failure.

A presumable cause of the activation of the osteoclasts is that titanium and the titanium alloy do not have sufficient affinity for bone cells. On a surface of a material which does not have sufficient affinity for the bone cells, differentiation from osteoclast precursor cells to the osteoclasts is accelerated to cause osteolysis. It has been known that titanium and the titanium alloys have relatively high affinity for the bone cells. However, their affinity is not sufficient, and the dental implant failure may occur depending on conditions of the jaw bone and an oral cavity of a subject.

To improve the affinity for the bone cells, coating the implant such as the dental implant etc. with a diamond-like carbon thin film (a DLC film) has been attempted (see, e.g., Patent Document 1). The DLC film has high biocompatibility because a main component thereof is carbon, and a surface thereof is smooth and inactive. For these reasons, the DLC film presumably has high affinity for the bone cells.

CITATION LIST

Patent Document

[Patent Document 1] Japanese Patent Publication No. 2002-204825

Non-Patent Document

[Non-Patent Document 1] Muhbalt L. et al., "Int J Oral Maxillofac Implants," 1989, vol. 4, pp. 125-130

SUMMARY OF THE INVENTION

Technical Problem

The dental implant coated with the DLC film has the following disadvantages. First, the DLC film is hard and rigid, and cannot sufficiently adhere to the base material. Thus, the DLC film may be peeled off the base material, or may be cracked. An intermediate layer may be formed to improve adhesion between the DLC film and the base material. However, it is said that a load applied to the dental implant is as high as 300 N (see, e.g., Non-Patent Document 1). With such a large load applied to the dental implant, the peeling and cracking of the DLC film cannot be prevented by merely forming the intermediate layer.

In an intraoral environment, acid etc. enters the DLC film when the DLC film is peeled off or slightly cracked. This may lead to corrosion of the base material, or may accelerate the peeling of the DLC film, thereby significantly reducing durability of the dental implant. Thus, preventing the cracking is of great importance to provide the dental implant coated with the DLC film.

Although antithrombogenicity, adhesion to cells, and cytotoxicity of the DLC film have been studied, influence of the DLC film on the differentiation from the osteoclast precursor cells to the osteoclasts has not been studied.

The disadvantages described above may arise in other implants than the dental implants to which a large load is applied, and high affinity for the bone cells is required, e.g., dental materials such as artificial teeth and crown restorations, artificial bones, artificial joints, etc.

To solve the disadvantages, the present disclosure is intended to provide an implant material which can reduce the differentiation from the osteoclast precursor cells to the osteoclasts, and is resistant to degradation even when a large load is applied.

Solution to the Problem

To accomplish the intention, an implant material of the present disclosure includes a carbon thin film which coats a surface of a base material of the implant material, and contains a silicon carbide component.

Specifically, the disclosed implant material includes: a base material; and a carbon thin film which is formed on a surface of the base material, and contains silicon, wherein the carbon thin film contains a C—C component in which carbon atoms are bonded, and a SiC component in which carbon and silicon atoms are bonded, and a ratio of the SiC component is 0.06 or higher.

The disclosed implant material includes the carbon thin film formed on the surface of the base material. This can reduce differentiation from osteoclast precursor cells to osteoclasts, and can provide high affinity for bone. Since the carbon thin film contains the SiC component, the carbon thin film has a lower elastic coefficient than general carbon thin films. Thus, the carbon thin film is resistant to peeling off the surface of the base material, and to cracking. Therefore, the implant material can be resistant to degradation even when excessive stress, such as occlusal force etc., is applied thereto.

In the disclosed implant material, the ratio of the SiC component is preferably 0.5 or lower.

In the disclosed implant material, the base material may be metal. The base material may be a dental implant, an artificial tooth, or a crown restoration.

A method for manufacturing the disclosed implant material includes: preparing a base material for implant; removing moisture from a chamber in which the base material is placed; and introducing material gas as a carbon source and a silicon source into the chamber after the preparation of the base material to form a carbon thin film containing a C—C component in which carbon atoms are bonded, and a SiC component in which carbon and silicon atoms are bonded on a surface of the base material by ionized deposition.

The disclosed method for manufacturing the carbon thin film includes the removal of moisture from the chamber. Thus, a carbon thin film containing less silicon oxide component can be formed even when an amount of silicon introduced in the chamber is increased. This can provide an implant material which has high affinity for bone cells, and is resistant to peeling off the surface of the base material, and to cracking.

Advantages of the Invention

According to the disclosed carbon thin film, and the method for manufacturing the same, the implant material which reduces the differentiation from the osteoclast precursor cells to the osteoclasts, and is resistant to degradation even when a large load is applied thereto can be provided.

BRIEF DESCRIPTION OF THE DRAWINGS

FIG. 4(a) shows evaluation of expression of TRAP, and FIG. 4(b) shows evaluation of expression of cathepsin K.

DESCRIPTION OF EMBODIMENTS

Figure 1A:
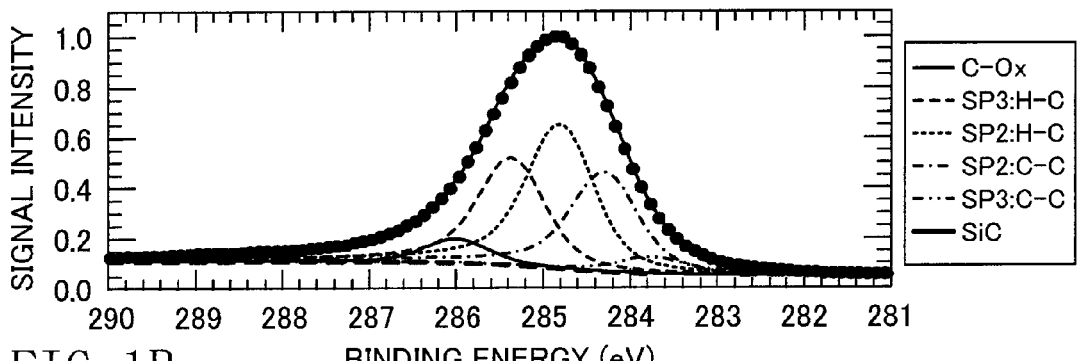
FIGS. 1(a)-1(d) are charts showing C1s spectra obtained by XPS analysis of samples of an example of the present invention.
Figure 1B:
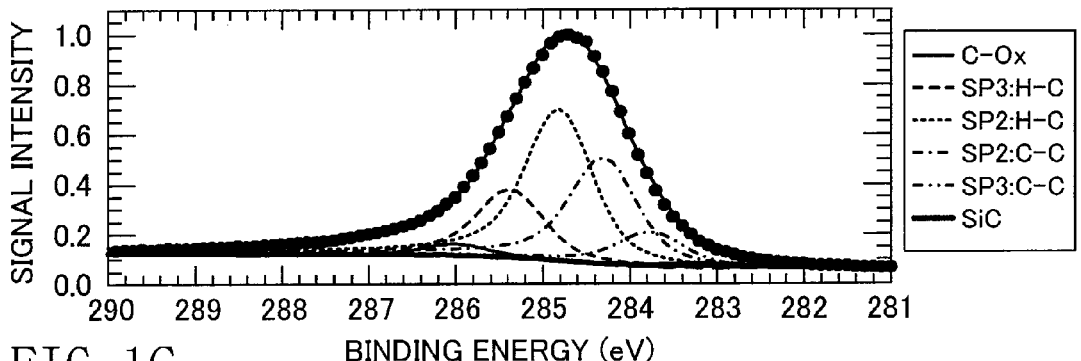
Figure 1C:
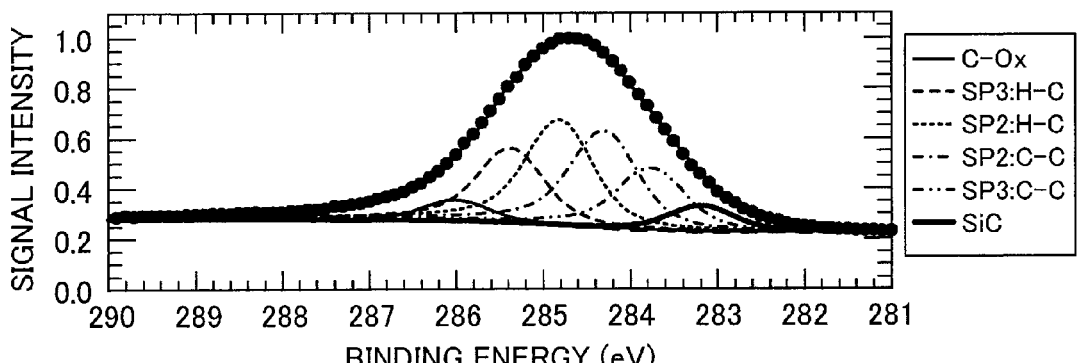
Figure 1D:
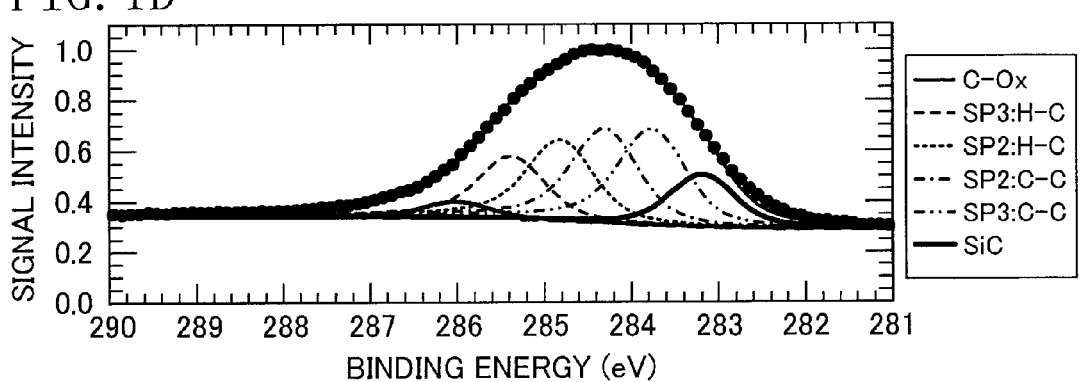

An implant of an embodiment of the present invention is a dental implant. The dental implant of the present embodiment includes a base material made of titanium etc., and a carbon thin film which coats a surface of the base material. The carbon thin film is a material represented by a diamond-like carbon thin film (a DLC film) which is an amorphous film made of SP2 bonded carbon, and SP3 bonded carbon. The diamond-like carbon thin film generally contains hydrogen (H), and oxygen (O) in addition to carbon. When silicon (Si), fluorine (F), etc. are supplied in depositing the carbon thin film, the carbon thin film can contain these elements in various ratios.

Studies on properties required for the carbon thin film which coats the surface of the dental implant will be described below.

It is said that a load applied to the dental implant is as high as 300 N. When a load of 300 N is applied to a dental implant of a general shape having a screw diameter of 2.7 mm, and an effective engagement length of 5 mm, a load of about 7.1 N/mm$^2$ is applied to a threaded portion of the screw. Pure titanium has a Young's modulus of 106 GPa. Thus, a distortion rate of the threaded portion of the dental implant is $6.6 \times 10^{-3}$%. The material coating the surface of the dental implant has to be resistant to cracking even when the material experiences distortion greater than the above-described distortion.

To ensure affinity for bone cells, the material has to be able to reduce differentiation from osteoclast precursor cells to osteoclasts. Further, the material has to be resistant to corrosion in an intraoral environment.

The inventors of the present invention have found that a Si-added carbon thin film is significantly suitable as a material which satisfies the above requirements. When Si is added in depositing the carbon thin film, the carbon thin film can contain a carbon-carbon (C—C) bond in which general carbon atoms are bonded, and a silicon carbide (SiC) component in which carbon and Si atoms are bonded. The Young's modulus of the carbon thin film greatly varies depending on the content of the SiC component. This can provide the carbon thin film which is resistant to the cracking.

When Si is added, a silicon oxide ($SiO_2$) component is introduced into the carbon thin film. Increase in $SiO_2$ component decreases resistance of the carbon thin film to corrosion. To prevent the cracking without reducing the resistance to corrosion, production of the $SiO_2$ component has to be prevented while introducing the SiC component introduced into the carbon thin film.

The $SiO_2$ component in the carbon thin film is produced when Si and oxygen supplied from an atmosphere are reacted in depositing the carbon thin film. A major source of oxygen is moisture. Thus, when the carbon thin film to which Si is added in a dehydrated condition is formed on the surface of the base material, the implant can be provided with high affinity for the bone cells, and high durability. Specifically, the carbon thin film preferably contains Si, and the $SiO_2$ component in a ratio of 0.05 or lower.

The implant will be described in detail below by way of an example.

EXAMPLE

Examination of Physical Properties

Various types of carbon thin films were formed on the surface of the base material to examine relationship between a composition and a physical property such as Young's modulus of each film.

For the examination of the physical property, a stainless (JIS standard: SUS316) wire having a diameter of 0.5 mm was used as the base material. The base material was placed in a chamber of an ionized deposition apparatus, and bombardment was performed for 30 minutes. The bombardment was performed by introducing argon (Ar) gas into the chamber to a pressure of $10^{-1}$ Pa-$10^{-3}$ Pa ($10^{-3}$ Torr-$10^{-5}$ Torr), generating Ar ions by discharge, and allowing the generated Ar ions to impact on the surface of the base material.

With benzene and tetramethylsilane ($Si(CH_3)_4$) being introduced in the chamber, discharge was performed for 5-10 minutes to form a carbon thin film, which is a 100 nm thick amorphous DLC film containing silicon (Si) and carbon (C) as main components. Various types of carbon thin films having different Si contents were formed by changing the amount of tetramethylsilane introduced.

Before forming the carbon thin film, the chamber was heated to 80° C. to perform baking for 2 hours. Thus, moisture remaining in the chamber was removed to reduce the production of $SiO_2$ due to oxidation of Si during the deposition. The $SiO_2$ component in the surface of the carbon thin film can be reduced by stacking another carbon thin film in which the composition is changed not to contain Si on the carbon thin film. However, this complicates the deposition of the film. Further, the upper carbon thin film may be peeled off the lower carbon thin film at an interface therebetween.

The composition of the carbon thin film was analyzed by X-ray photoelectron spectroscopy (XPS). An X-ray photoelectron spectrometer JPS9010 manufactured by JEOL Ltd. was used. Measurement was performed using an AlKα ray (1486.3 eV) as an X-ray source at an acceleration voltage of 12.5 kV and an emission current of 15 mA in a vacuum of $8 \times 10^{-7}$ Pa. The measurement was performed on a region of a diameter of 5 mm selected at random. A detector was inclined at 75° with respect to a perpendicular direction to obtain composition information from a depth of about 5 nm.

Background of the obtained spectrum was removed by Shirley method. In measuring the sample, precision of the analysis is affected by a charge shift of 0.2 eV. Thus, gold nanoparticles were dropped on part of a surface of the sample and dried to obtain a shift from binding energy of gold (Au4f7/2) to correct the charge shift.

A ratio of the SiC component with respect to total carbon in the sample [SiC]/[C] was obtained by curve fitting of a C1s spectrum. First, the C1s spectrum was divided into four spectral components of SP3 carbon-carbon bond (SP3:C—C), graphite carbon-carbon bond (SP2:C—C), SP3 carbon-hydrogen bond (SP3:C—H), and SP2 carbon-hydrogen bond (SP2:C—H). The spectral components had peaks of 283.7 eV-283.8 eV, 284.2 eV-284.3 eV, 284.7 eV-284.8 eV, and 285.3 eV-285.4 eV, respectively. A peak remaining in a lower energy region was considered as a carbon-silicon bond (SiC), and a peak remaining in a higher energy region was considered as a carbon-oxygen bond (C—Ox). A peak of the SiC component was 283.1 eV-283.2 eV. A ratio between integrated intensity of total carbon obtained from the C1s spectrum and integrated intensity of the SiC component was regarded as the ratio of the SiC component [SiC]/[C].

The ratio of the $SiO_2$ component in the surface of the sample was measured by a surface sensitive technique, i.e., by inclining a detector of photoelectrons at an angle of 75° relative to the surface of the sample. A ratio of concentration between Si and C ([Si]/([Si]+[C])) was calculated from the obtained C1s and Si2p spectra using a relative sensitivity coefficient. Integrated intensity of the $SiO_2$ component was obtained by curve fitting of the Si2p spectrum. A ratio between integrated intensity of total Si obtained from the Si2p spectrum and integrated intensity of the $SiO_2$ component was multiplied with the ratio of concentration between Si and C to obtain a ratio of $SiO_2$ component $[SiO_2]/([Si]±[C])$. FIGS. 1(a)-1(d) show C1s peaks of the obtained samples measured by XPS and the curve fitting results. Si contents in the samples shown in FIGS. 1(a)-1(d) obtained by Auger electron spectroscopy were 0%, 3%, 19%, and 27%, respectively. The Auger electron spectroscopy was performed using a scanning Auger electron spectrometer PHI-660 manufactured by PHYSICAL ELECTRONICS. An acceleration voltage of an electron gun was 10 kV, and a sample current was 500 nA. An acceleration voltage of an Ar ion gun was 2 kV, and a sputtering rate was 8.2 nm/min.

As shown in FIGS. 1(a)-1(d), a ratio of the peak of SiC gradually increased with the increase in Si content. The ratios of the SiC component [SiC]/[C] obtained by the curve fitting were 0, 0.004, 0.064, and 0.13, respectively. A value $[SiO_2]/([Si]+[C1])$ was 0.015 or lower in every sample.

The Young's modulus of each of the obtained samples was measured. The Young's modulus was measured by nanoindentation using a diamond indenter in the shape of a 90° triangular pyramid equipped with a high sensitivity sensor (0.0004 nm, 3 nN) manufactured by Hysitron. Indentation was measured by using a scanning probe microscope (SPM) of Shimadzu Corporation, which can observe a three-dimensional shape of a surface of the sample with high magnification by scanning the surface of the sample with a fine stylet. For the nanoindentation, the diamond indenter was pressed into the sample while controlling the diamond indenter at a precision of 100 μN, and an elastic coefficient was quantified by analysis of a load displacement curve. The indenter was pressed for 5 seconds, and was pulled back for 5 seconds.

Figure 2:
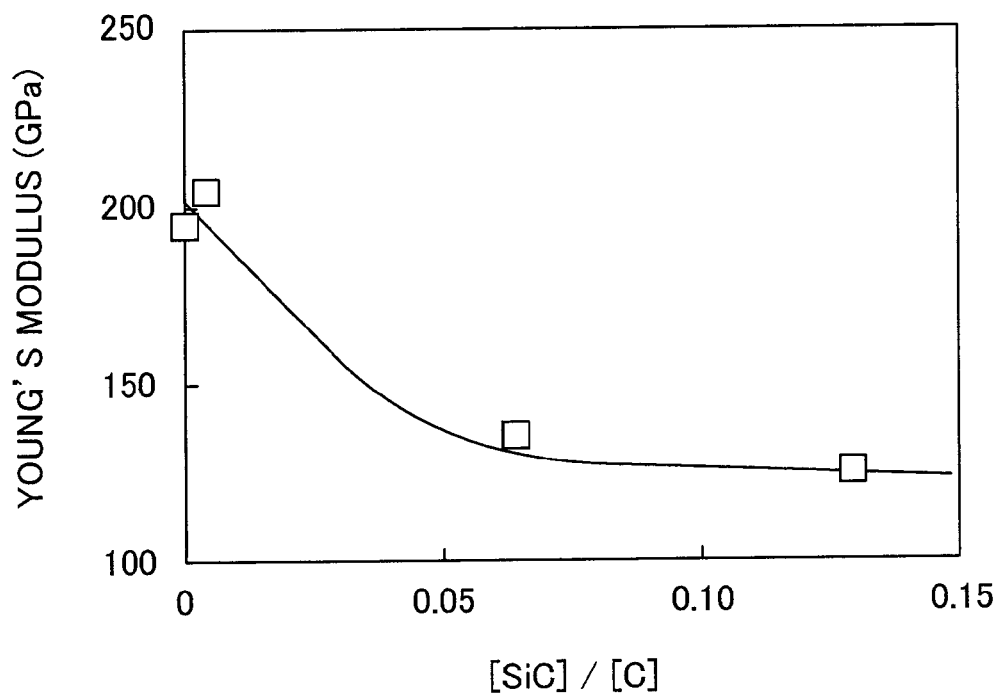
FIG. 2 is a graph illustrating relationship between a ratio of a SiC component and Young's modulus of the sample of the example of the present invention.

FIG. 2 shows relationship between the ratio of the SiC component [SiC]/[C] and the Young's modulus of the obtained sample. The Young's modulus abruptly decreased with the increase in the ratio [SiC]/[C], and was substantially constant after the ratio [SiC]/[C] increased to about 0.06.

The cracking due to distortion was then evaluated. The obtained sample was bent into an arc having a radius of 50 mm, and the bent portion was observed on a reflected electron image obtained by an electron microscope (TM-1000 of Hitachi, Ltd.).

Figure 3A:
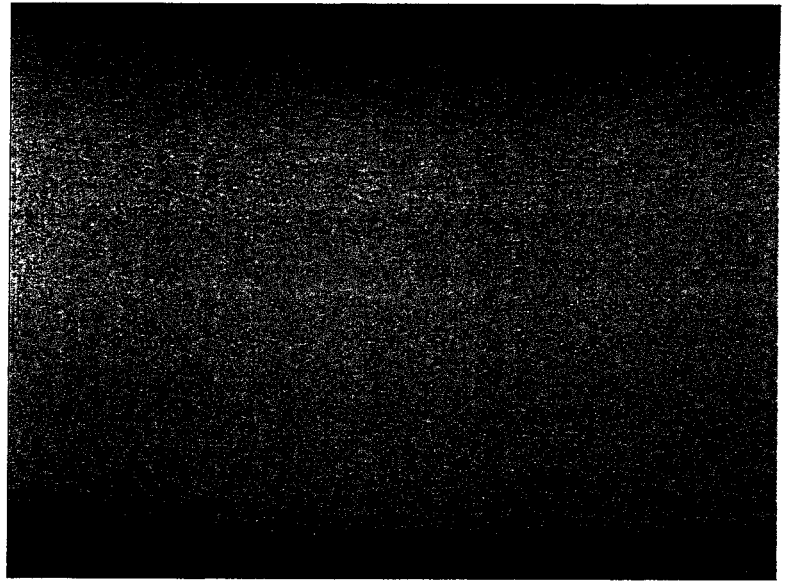
FIGS. 3(a) and 3(b) are electron micrographs illustrating the results of a bending test of the samples of the example of the present invention.
Figure 3B:
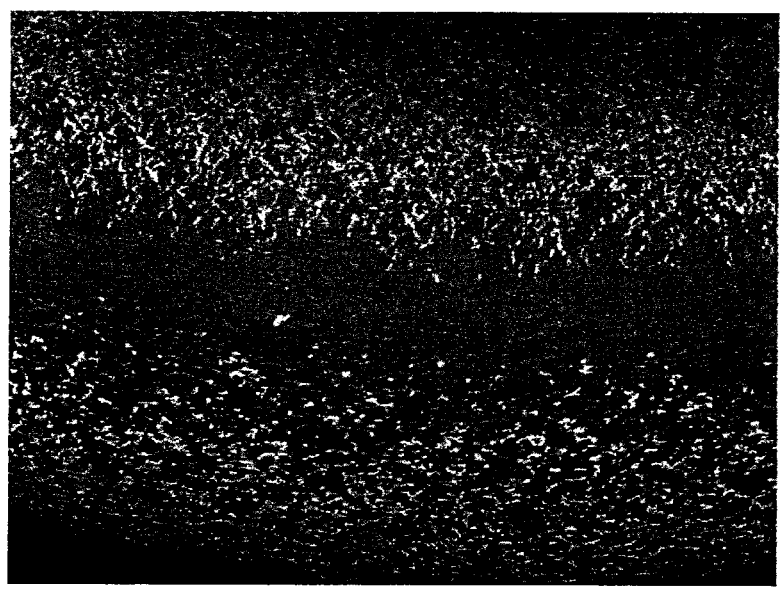

In FIG. 3(a) showing the electron image of the sample having the ratio [SiC]/[C] of 0.13, the peeling and cracking of the carbon thin film were not observed. In FIG. 3(b) showing the electron image of the sample having the ratio [SiC]/[C] of 0, fine cracks were generated in the carbon thin film, and the peeling of the film was observed.

As described above, the distortion rate of the dental implant is $6.6 \times 10^{-3}$%. When the wire having a diameter of 0.5 mm is bent into an arc having a radius of 50 mm, a distortion rate of an outer periphery of the arc is 0.25%. Thus, the carbon thin film having the ratio [SiC]/[C] of 0.13 can sufficiently be resistant to the cracking and peeling even when the carbon thin film experiences distortion greater than the distortion experienced by the threaded portion of the dental implant. The Young's modulus of the carbon thin film is substantially constant after the ratio [SiC]/[C] increased to 0.06 or higher. Thus, to prevent the cracking of the carbon thin film coating the surface of the dental implant, the ratio [SiC]/[C] is set to 0.06 or higher, preferably 0.1 or higher. However, excessive increase in ratio [SiC]/[C] affects the properties of the carbon thin film. Therefore, the ratio [SiC]/[C] is preferably 0.5 or lower.

Examination of Bone Compatibility

Bone compatibility of the carbon thin film formed on the surface of the base material was evaluated. To examine the bone compatibility, a sample prepared by forming a carbon thin film on a surface of a titanium plate was used. The carbon film used had the ratio [SiC]/[C] of 0.013.

The bone compatibility of the sample was evaluated by measuring differentiation to osteoclasts in the following manner. The sample and osteoclast precursor cells were brought into contact in the presence of an inducer of osteoclast differentiation (a receptor activator of NF-kB ligand: hereinafter referred to as RANKL), and were cultivated at 37° C. The osteoclast precursor cells used were cell line RAW264.7 cells (TIB-71, ATCC) which have been proved that they are differentiated to the osteoclasts in the presence of RANKL.

Then, expression of tartrate-resistant acid phosphatase (TRAP) and cathepsin K, which were differentiation related genes, was quantified by polymerase chain reaction (PCR) to evaluate the differentiation to the osteoclasts.

Figure 4A:
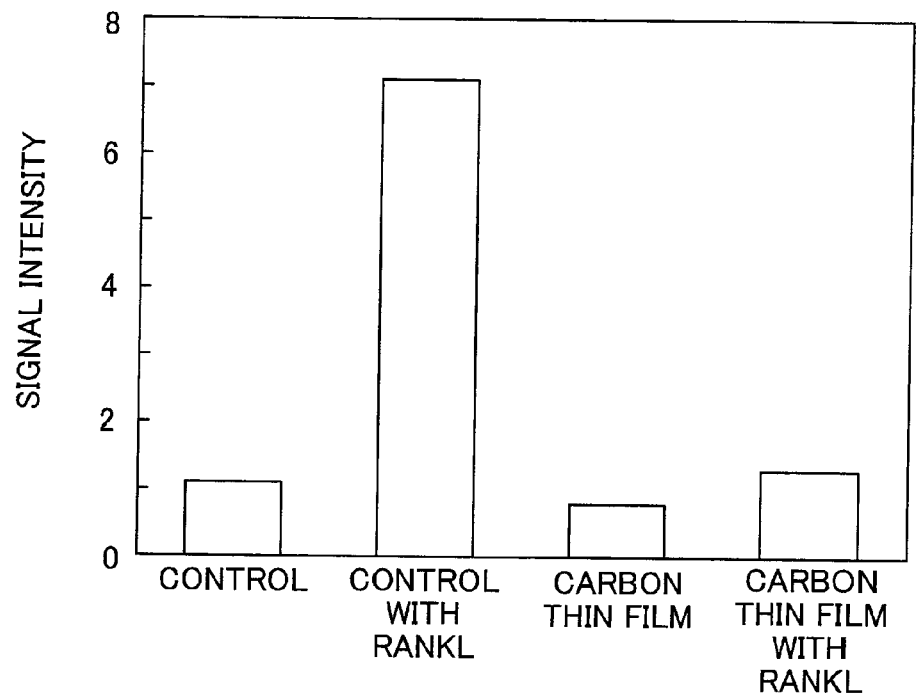
FIGS. 4(a) and 4(b) are graphs showing the evaluation results of bone compatibility of the samples of the example of the present invention, in particular.
Figure 4B:
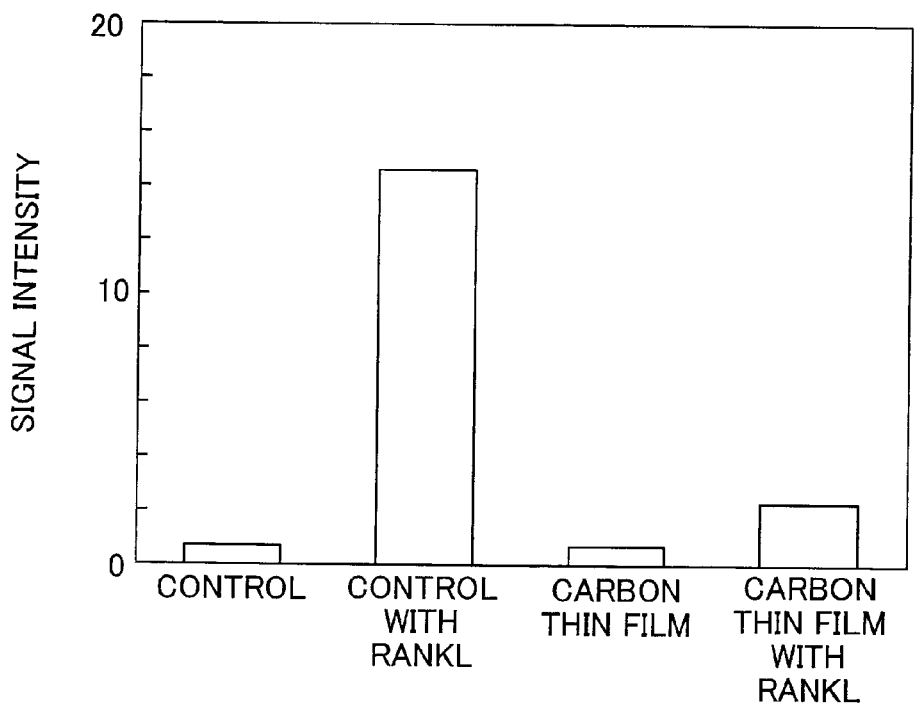

FIGS. 4(a) and 4(b) show the results of the quantification of the expression of the differentiation related genes as markers of the differentiation to the osteoclasts. FIG. 4(a) shows the results of the quantification of TRAP, and FIG. 4(b) shows the results of the quantification of cathepsin K.

In the absence of RANKL, the expression of TRAP and cathepsin K was hardly observed in both of a titanium plate as a control, and the titanium plate on which the carbon thin film was formed. That is, the RAW264.7 cells were hardly differentiated to the osteoclasts. In the presence of RANKL, however, the expression of TRAP and cathepsin K was observed on the titanium plate on which the carbon thin film was not formed, i.e., the RAW264.7 cells were differentiated to the osteoclasts. The expression of TRAP and cathepsin K was hardly observed on the titanium plate coated with the carbon thin film. This indicates that coating the base material with the carbon thin film can improve affinity for bone cells, and can reduce the differentiation from the osteoclast precursor cells to the osteoclasts.

In the above description, the dental implant has been described as an example. However, the implant of the example can be applied to artificial teeth etc. with similar bone compatibility and durability. Further, the implant of the example is suitable for a material of crown restoration and denture restoration because liquation of metal can be reduced.

The implant of the example can be applied not only to the dental materials, but to implants which are placed in living bodies, and to which the affinity for the bone cells is required, such as artificial bones, artificial joints, etc.

In the example, the carbon thin film was formed by sputtering. However, the carbon thin film may be formed by different methods. For example, DC magnetron sputtering, RF magnetron sputtering, chemical vapor deposition (CVD), plasma CVD, plasma ion implantation, superposed RF plasma ion implantation, ion plating, arc ion plating, ion beam deposition, or laser ablation may be used. The thickness of the carbon thin film is not particularly limited, but is preferably in the range of 0.005 pin-3 pin, more preferably in the range of 0.01 pin-1 pin.

The carbon thin film can directly be formed on the surface of the base material. However, for better adhesion between the base material and the carbon thin film, an intermediate layer may be provided between the base material and the carbon thin film. Various types of materials may be used as a material for the intermediate layer. For example, a known amorphous film made of silicon (Si) and carbon (C), titanium (Ti) and carbon (C), or chromium (Cr) and carbon (C). The thickness of the intermediate layer is not particularly limited, but is preferably in the range of 0.005 µm-0.3 µm, more preferably in the range of 0.01 µm-0.1 µm.

The intermediate layer can be formed by a known method, for example, sputtering, CVD, plasma CVD, metallizing, ion plating, arc ion plating, etc.

INDUSTRIAL APPLICABILITY

The disclosed carbon thin film, and the method for manufacturing the same can provide an implant material which can reduce differentiation from osteoclast precursor cells to osteoclasts, and which is resistant to degradation even when a large load is applied thereto. In particular, the disclosed carbon thin film, and the method for manufacturing the same are useful as dental materials, such as dental implants, artificial teeth, etc., to which affinity for bone cells is required, and a method for manufacturing the same.

What is claimed is:

1. A method for manufacturing an implant material comprising: preparing a base material for implant; removing moisture from a chamber in which the base material is placed; and introducing material gas as a carbon source and a silicon source into the chamber after the removal of the moisture to form a carbon thin film containing a C—C component in which carbon atoms are bonded, and a SiC component in which carbon and silicon atoms are bonded on a surface of the base material by ionized deposition, wherein
   the base material is made of metal,
   the removal of the moisture is performed by baking an inside of the chamber at 80° C. or higher, and
   a molar ratio of $SiO_2$ to the SiC component in the carbon thin film is 0.05 or lower.

2. The method for manufacturing the implant material of claim 1, wherein a molar ratio of the SiC component to the C—C component in the carbon thin film is 0.06 or higher and 0.5 or lower.

3. The method for manufacturing the implant material of claim 1, wherein a molar ratio of the SiC component to the C—C component in the carbon thin film is 0.1 or higher and 0.5 or lower.

4. The method for manufacturing the implant material of claim 1, further comprising:
   forming an intermediate layer made of silicon (Si) and carbon (C), titanium (Ti) and carbon (C), or chromium (Cr) and carbon (C) on the surface of the base material.

5. The method for manufacturing the implant material of claim 1, wherein the base material is a dental implant, an artificial tooth, or a crown restoration.

* * * * *